United States Patent [19]

Fumich

[11] Patent Number: 5,662,646

[45] Date of Patent: *Sep. 2, 1997

[54] METHOD AND APPARATUS FOR LASER SURGERY

[76] Inventor: Robert Mark Fumich, P.O. Box 397, Gates Mills, Ohio 44040

[*] Notice: The term of this patent shall not extend beyond the expiration date of Pat. No. 5,352,221.

[21] Appl. No.: 315,423

[22] Filed: Sep. 30, 1994

Related U.S. Application Data

[62] Division of Ser. No. 971,316, Nov. 4, 1992, Pat. No. 5,352,221.

[51] Int. Cl.$^6$ ............................................. A61B 17/36
[52] U.S. Cl. ............................... 606/15; 606/17; 607/89
[58] Field of Search .............................. 606/2, 15, 16, 606/17, 18; 607/88, 89

[56] References Cited

U.S. PATENT DOCUMENTS

| | | | |
|---|---|---|---|
| 3,865,113 | 2/1975 | Sharon et al. | 128/395 |
| 4,249,533 | 2/1981 | Komiya | 606/15 |
| 4,266,547 | 5/1981 | Komiya | 606/15 |
| 4,289,132 | 9/1981 | Rieman . | |
| 4,444,184 | 4/1984 | Oretorp . | |
| 4,503,853 | 3/1985 | Ota et al. | 606/16 |
| 4,520,814 | 6/1985 | Weeks . | |
| 4,638,800 | 1/1987 | Michel . | |
| 4,785,805 | 11/1988 | Joffe et al. | 606/15 |
| 4,834,729 | 5/1989 | Sjostrom . | |
| 4,917,084 | 4/1990 | Sinofsky | 606/16 |
| 5,030,217 | 7/1991 | Harrington | 606/14 |
| 5,037,421 | 8/1991 | Boutacoff et al. | 606/15 |
| 5,059,191 | 10/1991 | Beyer et al. | 606/2 |

FOREIGN PATENT DOCUMENTS 0 255 974 7/1987 European Pat. Off. .

OTHER PUBLICATIONS

Representative photocopies of Coherent Homium Laser with tip, manufactured by the Coherent Company.

*Primary Examiner*—Angela D. Sykes
*Assistant Examiner*—Sonya Harris-Ogugua
*Attorney, Agent, or Firm*—Fay Sharpe Beall Fagan Minnich & McKee

[57] ABSTRACT

An apparatus for use with a laser surgical tool comprises an elongate substantially hollow sheath having a pair of spaced apart axially extending guide members on a distal end and an attaching mechanism on the second end for ready attachment to a laser knife. The attaching mechanism is a grooved surface permitting rotation of the elongate sheath about its longitudinal axis which is coincident with the longitudinal axis of the laser knife. A second attaching mechanism comprises a plurality of circumferentially spaced apart, radially inwardly extending protuberances which matingly engage corresponding dimples on the laser knife preventing rotation of the sheath about the longitudinal axis. For use with laser knives having a bent elongate center portion, the sheath includes a separately rotatable guide sheath tip for rotation of that portion of the sheath between the bend in the elongate center portion of the laser knife and the distal end thereof, including the laser lens. All of the various sheath configurations are provided with axially extending guide pair members for receiving tissue therebetween during surgical procedures. The laser knife guide sheaths are discardable and formed of a flexible resilient material which is impervious to the laser light beam.

18 Claims, 3 Drawing Sheets

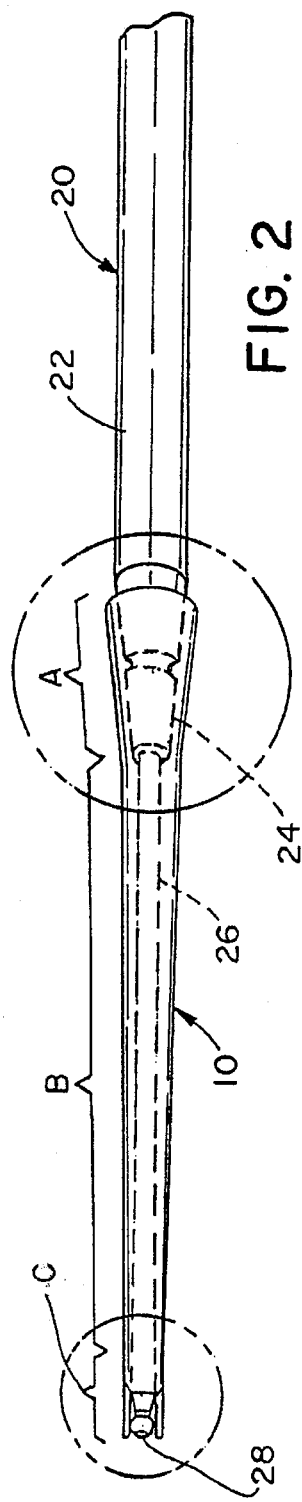
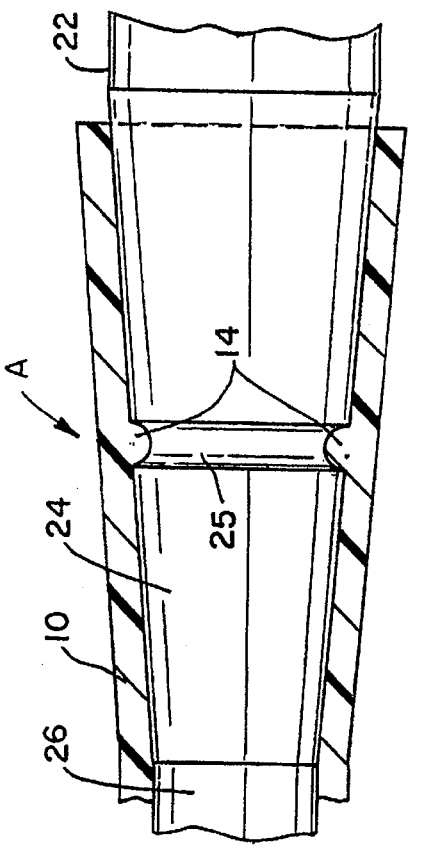
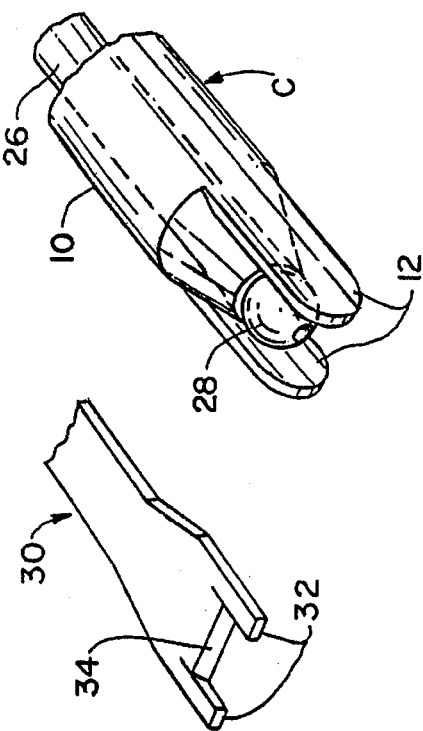

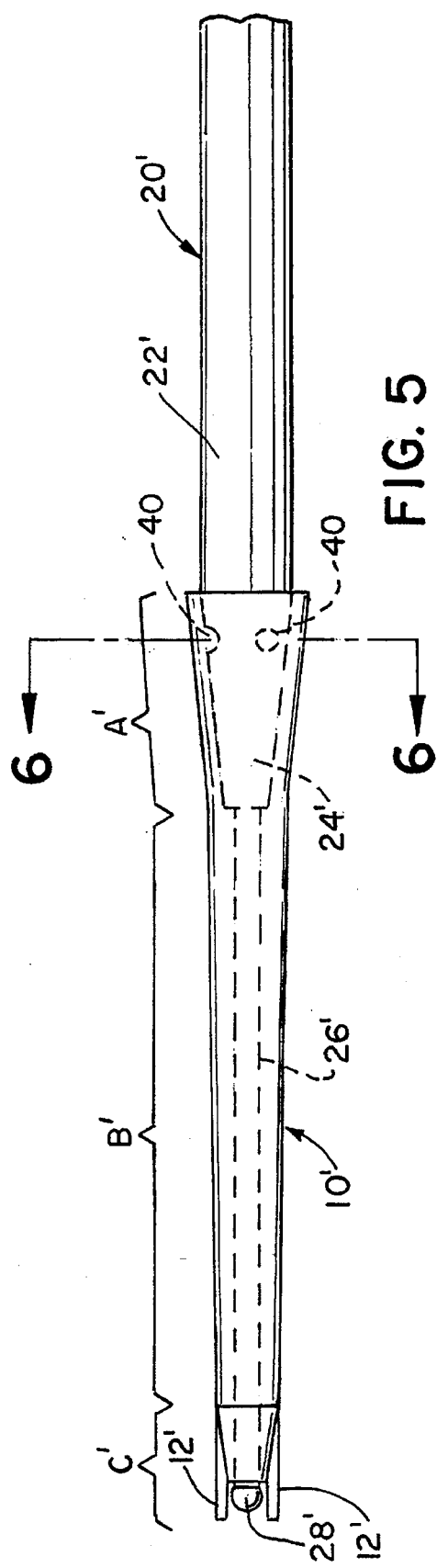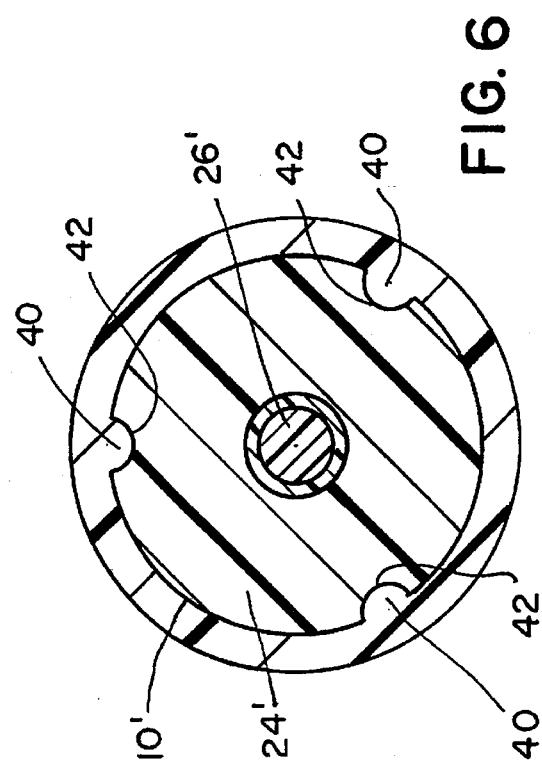

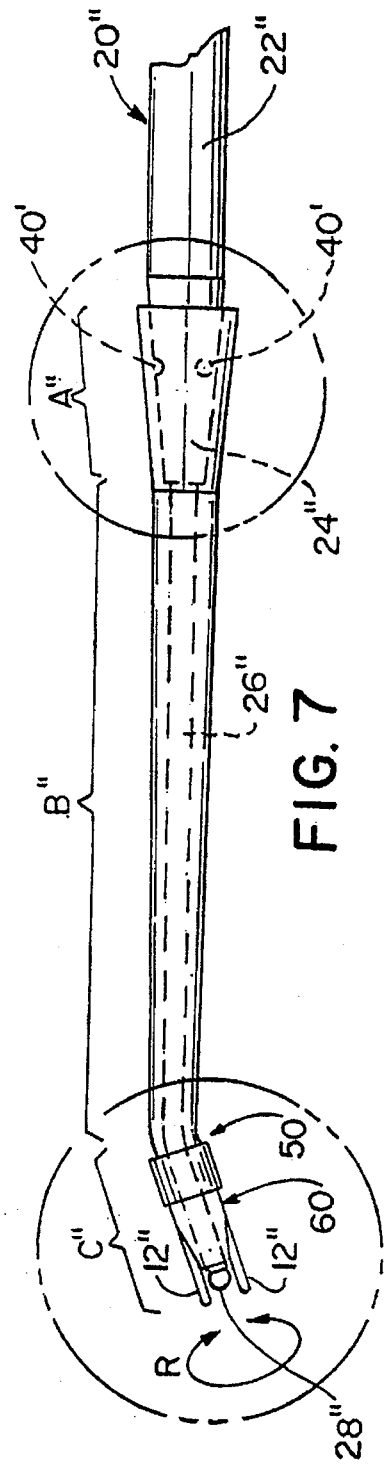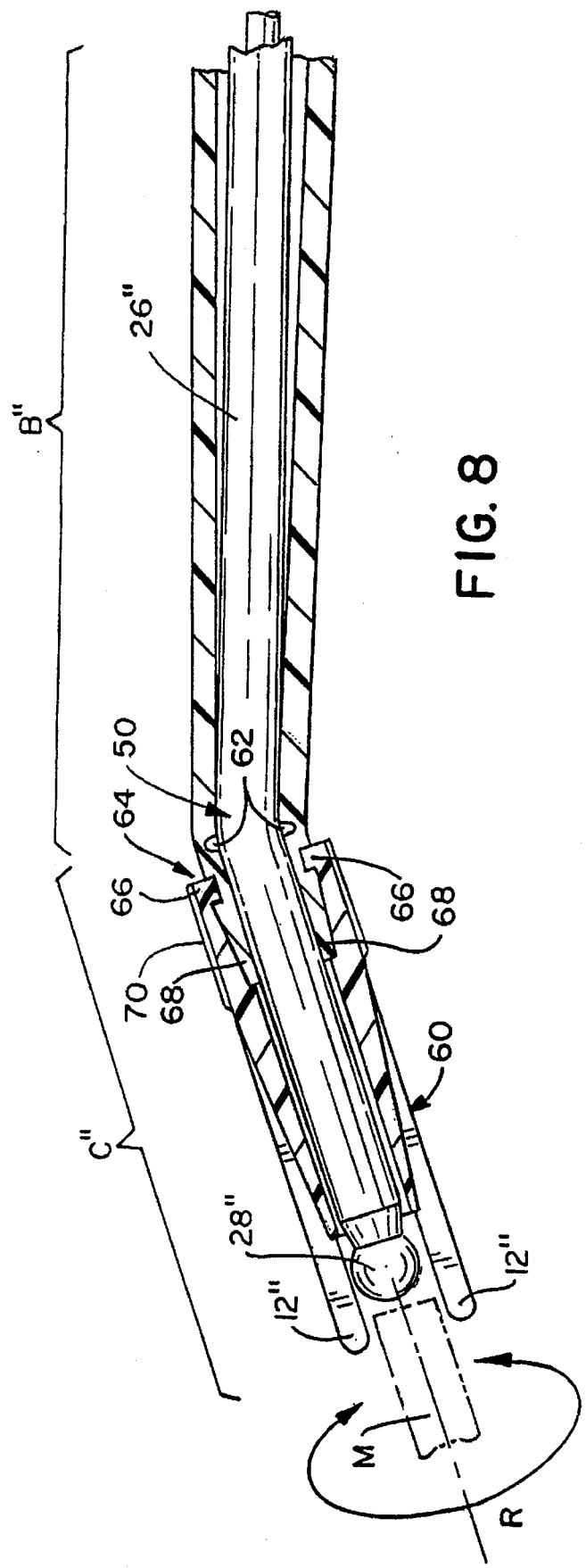

METHOD AND APPARATUS FOR LASER SURGERY

This application is a division of application Ser. No. 07/971,316, filed Nov. 4, 1992, now U.S. Pat. No. 5,352,221.

BACKGROUND OF THE INVENTION

This application pertains to the art of surgical instruments and specialized procedures using those instruments. More particularly, the application pertains to methods and apparatus for more easily and precisely using laser energy to perform surgical procedures such as arthroscopic meniscectomies and OB/GYN surgery including cervical procedures.

The invention is particularly adapted for use with laser-powered surgical tools and will be described with particular reference thereto, although it will be appreciated that the invention has broader application such as for use with other surgical tissue removal tools, including elongate fixed or rotatable blade knives or the like.

Meniscectomy tools have heretofore comprised simple surgical steel meniscectomy knives as taught in U.S. Pat. No. 4,289,132 and laser "knives" which use a laser light beam for ablating tissue to a selectable depth or beam penetration as taught in U.S. Pat. No. 5,037,421. An improvement over the fixed meniscectomy knife that has met with some acceptance in the surgical community comprises a rotatable tandem edged blade enclosed in an elongated sheath as taught in U.S. Pat. No. 4,834,729. The sheath is suitably provided with one or more circumferential openings on a distal end. By manipulating the knife, the tissue to be removed is received through the openings and encounters the rotating blades.

The surgical steel knives (non-laser) described above provide the surgeons with a certain "feel" by which continuous manual tactile feedback of the cutting edge position against the tissue is used to determine the correctness of the cut for proper tissue removal. Some surgeons find this tactile feedback highly desirable for certain procedures. However, laser knives in general do not provide much feedback. Thus, the laser knife is not used as frequently as one would expect.

One desirable feature of the laser knife not found in conventional knives, however, is the ability of the laser to precisely ablate tissue by heat vaporization. There is thus no need to subsequently withdraw or otherwise remove the severed tissue from the area. In addition, the depth of the "cut" is controllable by regulating the intensity and pulse width of the laser light beam itself. However, the laser knife does not provide the amount of tactile feedback as is obtainable using the traditional meniscectomy knives as described above. Also, the laser knives currently available do not conveniently permit the surgeon to see the depth of the cut. Because of these problems, many benefits of the laser instruments are missed by surgeons confident only in the use of traditional tools.

The present invention contemplates new and improved methods and apparatus which combine the benefits of traditional meniscectomy-type knives with the benefits of newly developed laser tissue ablating knives. The invention overcomes the above noted problems and provides an easy and inexpensive vehicle for obtaining tactile laser tip position feedback in a laser knife.

BRIEF SUMMARY OF THE INVENTION

In accordance with the present invention, there is provided an elongate hollow sheath adapted for close reception over a similarly elongate hollow laser knife for converting the knife into an improved laser knife with greater tactile feedback. A distal end of the sheath is provided with a pair of circumferentially spaced apart axially extending guides between which the tissue to be ablated is positively received. In use, the surgeon first slides a sheath over the laser tool until the two units lock in a manner set forth in greater detail below. Next, the distal end of the assembled apparatus is inserted into the patient and manipulated until the tissue to be removed is securely positioned between the pair of sheath guides. The surgeon is able to feel this relationship through the laser knife grip or handle with the sheath attached in place. With the distal end of the laser knife itself positioned immediately adjacent and in intimate contact with the tissue held between the guide pair, the laser beam is applied ablating the tissue according to known techniques. The surgeon can view the depth of the cut between the guide pair. The assembled apparatus is useful for removing a strip of the tissue edge by sliding the laser tip along the tissue edge held by the guide pair while simultaneously activating the laser light source.

A second form of elongate attachable sheath comprises an apparatus with a rotatable pair of axially extending guides. The rotatable guides enable the surgeon to variably position the body of the laser tool while maintaining constant contact between the distal end of the laser knife and the target tissue. The laser tool may be simultaneously rotated and/or dragged along the tissue's edge during which time the surgeon receives constant and uninterrupted feedback of the intimate contact relationship between the tissue and the tip of the assembled apparatus.

The principal object of the invention is the provision of a simple, inexpensive and effective safety tip apparatus for converting laser surgical tools into improved apparatus having the desired features of more traditional tools. This aids in the migration from older equipment to the more modern and efficient laser tools. The benefits ultimately inure to the patients.

A further object is the provision of an apparatus of the type described which includes rotatable, axially extending guide means for positively positioning a distal end of a laser cutting tool against the edge of tissue to be removed.

Yet another object is the provision of a laser safety tip guide means which is relatively inexpensive and disposable after use. The guide means is slidably receivable over standard laser cutting tools and discardable after use.

BRIEF DESCRIPTION OF THE DRAWINGS

The above and other objects and advantages will become apparent from the following description when read in conjunction with the accompanying drawings wherein:

FIG. 1 is an elevational view of an meniscectomy knife;

FIG. 2 is a side view of the first embodiment of the laser tool guide adapter sheath received over and locked onto a typical laser knife;

FIG. 3 is a first circled portion of FIG. 2 illustrating the distal end of the adapter sheath, including a pair of axially extending guide portions;

FIG. 4 is a longitudinal cross-section through the circled portion of FIG. 2 showing a latching mechanism for attachment of the sheath to the laser tool itself;

FIG. 5 is a side view of a second preferred laser tool guide adapter sheath received over and locked onto the laser knife of FIG. 2;

FIG. 6 is a cross-sectional view through the line marked 6—6 in FIG. 5;

FIG. 7 is a side view of yet another embodiment of the laser tool guide adapter sheath of the present invention received over and locked onto a typical laser knife with a bent elongate shaft portion; and, FIG. 8 is a longitudinal cross-sectional view of the circled portion of FIG. 7 illustrating the rotatable portion of the articulated sheath of FIG. 7.

DETAILED DESCRIPTION OF THE PREFERRED AND ALTERNATE EMBODIMENTS

Referring more particularly to the drawings wherein the showings are for the purpose of illustrating preferred embodiments of the invention only, and not for the purpose of limiting same, FIG. 2 illustrates a first preferred embodiment of the laser knife guide adapter sheath received over a traditional laser cutting knife. The guide sheath 10 is an elongate and substantially hollow cylinder adapted for close reception onto standard laser knives 20. The sheath 10 generally comprises three portions, including an attaching portion A, an elongate center portion B and a guide portion C. The sheath is suitably formed to substantially conform to the overall external size and shape characteristics of the laser knife 20, including a tapered portion 24, an elongate center portion 26, and a laser lens tip 28.

As can be appreciated, many different arrangements could be used for connecting the sheath 10 to the laser knife 20, however, in the preferred embodiment, the attaching portion A is associated with the tapered portion 24 of knife 20. The tapered portion 24 provides a transition between the elongate center portion 26 and a knurled grip 22. In this regard, as best shown in FIG. 4, tapered portion 24 is suitably provided with a circumferentially disposed radially inwardly extending groove 25. The guide sheath 10 is tapered to match the tapered portion 24 of the laser knife. Releasable attachment is provided by a circumferentially disposed and radially inwardly extending bead or raised portion 14 which correspondingly matches the groove 25 in the tapered portion 24 of the laser knife 20. As also illustrated in the FIGURES. The guide sheath 10 is coaxially received over the laser knife 20 permitting rotation about the common major longitudinal axis shared by the guide sheath and the laser knife. In this manner, the guide portion C is rotatable during use as will be described in greater detail below. In addition, the guide sheath itself is conveniently manually attachable over an appropriate laser knife and removable therefrom for disposal after use.

In the preferred embodiment, the sheath is a composite of plastic and titanium. Teflon or stainless steel may also be used as a substitute for the preferred titanium. Since portions of the sheath tip may be exposed to the laser light beam during use, titanium has been selected as the tip material for its imperviousness to the effects of the beam. However, as suggested above, the overall cost of the disposable sheath is a major consideration. This being the case, the preferred sheath embodiment comprises a substantially plastic hollow body with a titanium tip. The titanium tip is suitably joined to the plastic body during manufacture and may be recovered after the sheath is discarded for recycling. A second preferred embodiment of the sheath includes a composite tip. The composite tip comprises a thin layer of the titanium laminated over the plastic body forming the substantial majority of the guide tip itself. Since only the tip of the guide sheath is subjected to the laser beam, only the tip is laminated with the protective titanium. Teflon or stainless steel may also be used as a substitute for the preferred titanium. These arrangements reduces the overall cost of the guide sheath and is particularly important when the sheath is intended to be disposable. Of course, the entire guide sheath may be manufactured from the specialized metals but would be more expensive than the laminated guide portion described above. In any case, the sheath of the preferred embodiment is resiliently biased at the attaching portion A to the shape illustrated, but is reversibly deformable in order to permit the raised portion 14 to first slide over the tapered portion 24 and then snap into the groove 25, at which position the guide sheath is properly installed.

Turning now to the distal ends of both of the laser knife 20 and the guide sheath 20, and with particular further reference to FIG. 3, the guide portion C of the guide sheath is arranged to receivably engage tissue at the distal end of the laser knife during a surgical ablation process. To accomplish this, the guide portion C preferably comprises guide means positioned on the distal end of a surgical laser knife. More particularly, the guide means is at least one but preferably a pair of members disposed on opposite sides of the laser light output lens of a surgical laser knife and longitudinally extending beyond the distal end of the laser knife. In the preferred form this includes a guide pair 12 which axially extends from the sheath beyond the distal end of the laser knife as illustrated. Of course, the guide pair 12 may be incorporated as part of or permanently fixed to the tip of the laser knife itself. The guide pair is formed of a specialized metal such as titanium rendering it impervious to the laser beam as described above. Also, as indicated above, the guide pair 12 is suitably arranged to receive the edge of the tissue to be removed therebetween. For example, when the surgical procedure is a laser arthroscopic meniscectomy, the tissue is a meniscus and the spacing between the guide pair 12 is set to correspond to said meniscus. Similarly, the spacing is appropriately set for other tissues based on the procedure. When properly used, the tissue's edge is in intimate contact with both radially inwardly facing surfaces of the guide pair 12 and also with the laser lens 28 which emits a laser beam from a laser light source according to known methods. As illustrated in the FIGURE, the tips of the guide pair 12 are rounded. Further, the guide pair are sized to the circumference of the guide sheath body wherein each of the pair attach and extend to about one fourth of the circumference of the sheath. In use, the guide pair 12 functions as a safety apparatus wherein the surgeon closely monitors the progress of the procedure by viewing the depth of the cut through the pair 12.

As indicated above, the guide pair 12 provides the surgeon with both the benefits of the laser knife itself, as described above, and with an appropriate tactile tip position feedback as is provided by traditional meniscectomy knives 30 illustrated in FIG. 1. With reference to the old styled knife of that FIGURE in greater detail, a cutting edge 34 is provide between a mechanical guide pair 32 whereby the tissue to be removed is appropriately first positioned between the guide pair 32 by manual manipulation of the knife, and is thereinafter scrapped away by the surgeon using the cutting edge 34. The traditional meniscectomy knives 30 are somewhat awkward in use because it is not possible to rotate the handle portion (not shown) extending from the distal or cutting end during surgery while the guide pair 32 are engaged with the tissue. This is a severe constraint at times. The guide sheath of the preferred embodiment described above permits rotation of the guide pair about the common major longitudinal axis shared by the sheath and the laser knife.

In the those instances where manual rotation and other manipulations are not a major consideration, the embodiment illustrated in FIG. 5 presents a laser knife guide adapter sheath 10' substantially according to the first embodiment illustrated in FIG. 2 but with the addition of a plurality of circumferentially displaced, spaced apart protuberances at the attaching portion A' which match corresponding dimples on the tapered portion 24' of the laser knife 20'. FIG. 6 is a cross-sectional view through the attaching portion A' illustrated in FIG. 5 and illustrates another form of attaching the guide sheath 10' to the laser knife 20'. As illustrated, a plurality of circumferentially disposed radially inwardly extending protuberances 40 are provided on the guide sheath 10'. The protuberances 40 find corresponding mating structures on the laser knife 20' in the form of a plurality of circumferentially disposed, radially inwardly extending dimples 42. The attaching portion A' thus limits the sheath rotation.

The guide sheath of the embodiment illustrated in FIGS. 5 and 6 is formed of the same material as that set forth above regarding the first preferred embodiment of FIGS. 2–4. The above sheaths are similarly manually snap-installed by the surgeon prior to surgery. More particularly, the surgeon simply sides the guide sheath 10' over the distal end of the laser knife 20' until the plurality of protuberances 40 matingly engage the corresponding plurality of dimples 42. When each of the guide sheath protuberances or the bead 14 snap into position, the installation is complete. Obviously, the embodiment illustrated in FIGS. 5 and 6 provide a laser knife guide sheath 10' which includes a non-rotatable guide pair 12'. Accordingly, the behavior of this embodiment during surgery most closely resembles that of the prior art meniscectomy knife illustrated in FIG. 1. However, unlike the traditional steel knives, the laser knife with sheath presents a more versatile tool which leaves a substantially "cleaner" tissue edge due in part to the inherent superior cutting ability of the laser beam itself. The steel knives of old cut when force is applied along a path substantially aligned with the longitudinal axis of the tool through a handle portion (see FIG. 1 of U.S. Pat. No. 4,289,132). This makes it difficult to remove a strip of tissue along an edge perpendicular to the longitudinal axis of the tool. In contradistinction, the apparatus of the preferred embodiments are particularly well adapted for performing the procedure set forth immediately above and other similar surgeries.

Also, the guide sheath 10' of the instant invention is disposable after use and is customizable according to intended application. In that regard, the distance between the guide pair 12' may be varied. A set of laser knife guide sheaths 10' may include a plurality of different sizes wherein for each size, the distance between the guide pair "fingers" is incrementally varied from a small spacing to large spacing. The surgeon then merely selects a sheath having an appropriate guide pair spacing for the intended application, installs the guide sheath over a standard laser knife and commences with the surgery at hand. Alternatively, a first sheath may be substituted with a second during a single surgical procedure as necessary. Of course, as must be appreciated, the above features are equally applicable to each of the various embodiments discussed herein.

With reference next to FIGS. 7 and 8, yet another embodiment of the laser tool guide adapter sheath is illustrated for use with a laser knife having a distinct and pronounced bend in its elongate center portion.

With reference to those FIGURES in greater detail, it is apparent that the guide portion C" has been somewhat modified to account for the bend 50 in the elongate center portion 26" of the laser knife 20". With special reference to FIG. 8, the elongate center portion B" of the sheath is provided with a circumferentially disposed, diminishingly outwardly extending flex groove 62 which aids in articulating the sheath between the guide portion C" and the elongate center portion B". The flex groove 62 is suitably disposed axially along the length of the sheath to coincide with the bend 50 in the elongate center portion 26" of the laser knife 20".

Downward (toward the distal end) from the flex groove 62, the sheath is formed into a tapered bearing surface 68 for engagement with a rotatable guide sheath tip 60 to be described below. Between the tapered bearing surface 68 and the flex groove 62, a circumferential inwardly extending square groove 64 is disposed for receiving a corresponding circumferential inwardly extending square tongue 66 comprising part of the rotatable guide sheath tip 60. Lastly, a lock nut 70 threadedly engages the rotatable guide sheath tip 60 in the area near the tapered bearing surface 68 longitudinally locking sheath tip 60 in place. The tip 60 is replaceable in the manner set forth above regarding the sheath of FIGS. 2 and 5. However, in the instant embodiment, the elongate center and attaching portions B", A" remain connected to the laser knife since only the tip 60 carries the guide pair 12".

The rotatable guide sheath tip 60 includes a guide pair 12" for receiving the tissue to be ablated M therebetween. The tips are titanium in the preferred embodiment but may be laminated with other specialized metals as described above and are thereby made impervious to the laser beam. The guide sheath tip 60 is rotatable about an axis in a rotational direction R for easy manipulation of the overall assembled apparatus during use. For the purposes of illustration, the FIGURE illustrates a tissue edge M inserted between the guide pair 12" and against the laser lens 28". In this position, the grip portion 22" of the laser knife 20" may yet be rotated and/or otherwise manipulated while the laser lens 28" maintains intimate contact with the tissue M held between the guided pair 12".

Further, during use, the laser lens 28" is dragged across the tissue edge M while the tissue is held in place by the guide pair 12" and the laser beam is actuated to "scrape" tissue in a direction which would be in or out of the page as viewed in FIG. 8 (in the plane of the rotational direction R). Also, while the laser cutting tool is dragged along the edge of the tissue M, the knurled grip portion 22" is suitably rotatable during the course of tissue ablation. Thus, according to the apparatus of the third embodiment set forth above, it is possible to simultaneously linearly translate and angularly rotate the laser lens 28' while maintaining intimate contact between the lens and the tissue while the guide pair ensures same providing constant tactile tip position feedback during the course of a surgical procedure.

When the apparatus is used in OB/GYN cases, particularly cervical procedures, the sheath is rotated in a circular direction protected by the tips 12 as the laser knife tip is passed along the cervix opening, to perform a simple and safe conization of the cervix.

In an alternative, the rotatable guide sheath tip 60 is part of the elongate center portion B" dispensing with its tapered bearing surface 68 and the lock net 70. In this embodiment, the flex groove 62 functions as a "universal" for rotatably connecting the guide portion C" to the center portion B". The attaching portion A" is rotatable as illustrated in FIG. 4 wherein the entire guide sheath is thus rotatable from the attaching portion, through the center portion, including the flex groove 62 and the guide tip 12". The tips 12" are laminated with titanium as described above.

As indicated above regarding the spacing between the guide pairs, it is also apparent that the rotatable guide sheath tip 60 is interchangeable with a plurality of similar sheath tips having appropriately sized guide pair spacings. The surgeon merely selects an appropriate guide sheath tip for the intended application beforehand or "on the fly" during a single surgical procedure.

A further advantage of the apparatus set forth in FIGS. 7 and 8 is the ability for the surgeon to approach the tissue M with the sheath tip 60 in an appropriate position for receiving the tissue between the guide pair regardless of the angular position of the laser knife 20" due to the rotatability of the tip 60 about the rotational axis in an orbit R.

The invention has been described with reference to the preferred embodiments. Obviously, modifications and alterations will occur to others upon a reading and understanding of this specification. It is intended to include all such modifications and alterations insofar as they come within the scope of the appended claims or the equivalents thereof.

Having thus described the invention, I now claim:

1. A method of laser surgery for tissue ablation using an elongate laser knife emitting a laser light at a first distal end and having a manual grip, the method comprising the steps of:
   receiving a guide sheath over said first end of the laser knife;
   fastening said guide sheath to said grip by engaging a first surface of said guide sheath with a first surface of said grip;
   moving said first distal end of the laser knife toward said tissue guided by a pair of spaced apart guide members on a first end of the sheath; and,
   ablating said tissue with said laser light emitted from the laser knife when said first distal end is positioned proximate said tissue received between the sheath guide members.

2. The method according to claim 1, wherein the fastening step includes connecting the guide sheath to the grip by engaging a first circumferential bearing surface of the grip with a corresponding first circumferential bearing surface of the sheath.

3. The method according to claim 2, further comprising rotating the elongate laser knife about its longitudinal axis while said tissue is received between the sheath guide members.

4. The method according to claim 1, wherein the fastening step includes connecting the guide sheath to the grip by engaging a plurality of circumferentially spaced-apart dimples on the grip with a corresponding plurality of spaced-apart protuberances on the sheath.

5. The method according to claim 1 wherein:
   the moving step includes moving the first distal end of the laser knife toward an edge of a substantially planar tissue; and,
   the ablating step includes advancing said first distal end of the laser knife along said edge of the substantially planar tissue.

6. The method according to claim 5, further comprising rotating the elongate laser knife about its longitudinal axis while said tissue is received between said spaced apart guide members on the first end of the sheath.

7. The method according to claim 1, wherein the fastening step includes connecting the guide sheath to the grip by engaging a plurality of circumferentially spaced-apart protuberances on the grip with corresponding plurality of spaced-apart protuberances on the sheath.

8. A safety guide apparatus in combination with an elongate contact surgical laser knife including a distal end emitting a laser light beam ablating tissue contacting said distal end, the safety guide apparatus comprising:
   attaching means for selectively releasably attaching the apparatus to said contact laser knife; and,
   an end member means connected to the attaching means and extending at least in part beyond the distal end of said contact laser knife, for positioning said tissue contacting said distal end.

9. The safety guide apparatus according to claim 8 wherein said end member comprises a pair of spaced apart guide members axially extending beyond the distal end of the knife.

10. The safety guide apparatus according to claim 9 wherein the pair of spaced apart guide members are disposed on the attaching means on opposite sides of the distal end of the laser knife.

11. The safety guide apparatus according to claim 8 wherein the attaching means comprises means for rotatably receiving said end member.

12. The safety guide apparatus according to claim 11 wherein the receiving means comprises connection means for receiving said end member for free rotation of the end member about the longitudinal axis of said elongate surgical laser knife.

13. A method of laser surgery on tissue using an elongate laser tool having a distal end axially emitting a laser light and having a manual grip, the method comprising the steps of:
   receiving a guide sheath having a pair of spaced apart guide members, over said first end of the laser tool;
   fastening said guide sheath to said grip by engaging first surface of said guide sheath with a first surface of said grip:
   receiving said tissue between the pair of spaced apart guide members on said laser tool, the pair of spaced apart guide members extended beyond said distal end in said axially emitting direction;
   contacting said distal end against said tissue while least one of said pair of spaced apart guide members contacting said tissue; and,
   emitting said laser light from said distal end at said tissue.

14. The method according to claim 13 further comprising the step of axially moving said distal end of said laser tool toward said tissue while contacting said tissue with said at least one of said spaced apart guide members.

15. The method according to claim 14 further comprising the step of sliding said tool along an edge of said tissue while said distal end and said at least one of said spaced apart guide members are both contacting said tissue.

16. The method according to claim 15 further comprising the step of rotating said elongate laser tool about its longitudinal axis while both i) sliding the tool along said tissue edge and ii) contacting said distal end and said at least one of said spaced apart guide members against said tissue.

17. The method according to claim 13 further comprising the step of sliding said tool along an edge of said tissue while said distal end and said at least one of said spaced apart guide members are both contacting said tissue.

18. The method according to claim 13 further comprising the step of rotating said elongate laser tool about its longitudinal axis while both i) sliding the tool along said tissue and ii) contacting said distal end and at least one of said spaced apart guide members against said tissue.

* * * * *